Sept. 27, 1949. M. C. ALLWOOD Plant Pat. 876
CARNATION PLANT
Filed July 21, 1948
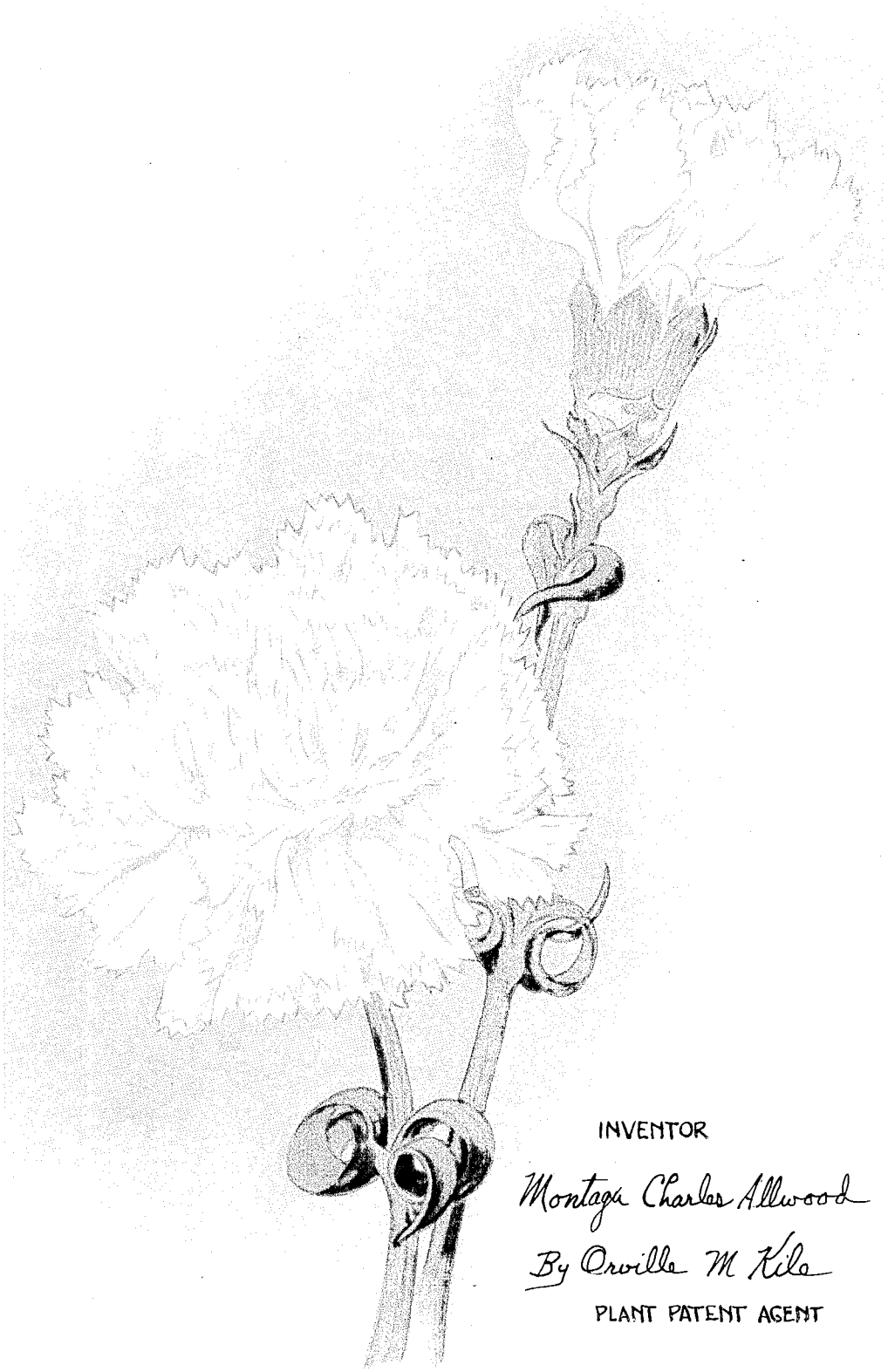
INVENTOR
Montague Charles Allwood
By Orville M Kile
PLANT PATENT AGENT Patented Sept. 27, 1949

Plant Pat. 876

UNITED STATES PATENT OFFICE

876

CARNATION PLANT

Montagu Charles Allwood, Sussex, England, assignor to Charles H. Totty Co., Inc., Madison, N. J.

Application July 21, 1948, Serial No. 39,852

1 Claim. (Cl. 47—60)

My present invention pertains to a new and distinct variety of carnation plant of the perpetual flowering type and resulted from definite breeding efforts made by me at our greenhouses at Wivelsfield Nurseries in Sussex, England. The parents of the new variety are an unnamed white seedling and Allwood's Purity.

The outstanding feature of this new plant is the flower which combines great size with "perfect" form. Also notable are the rich clove fragrance, the broad strong calyx, springiness of calyx claws, and heavy substance of the petals, as well as the rapidity with which the plant produces these large flowers.

Asexual reproduction has proved the distinctive qualities to be permanently fixed.

Illustrations accompanying these specifications show three specimens of the flower of this new variety in varying stages of opening, together with some of the foliage and stems, in approximately true colors. Special attention is given to showing the calyx.

Following is a detailed description of the plant and flower of my new variety. Color designations refer to the ordinary dictionary meaning except where plate references are made, and these indicate Ridgway's Color Standards and Nomenclature.

*The plant*

Growth habit: Very free-growing, producing large plants.

Blooming habit: Continuous bloomer; exceedingly productive. Produces large flowers more quickly than any other known variety of carnation.

Stems:

*Internodes.*—Short to medium (1¾ to 3 inches), allowing foliage to come close together.

*Color.*—Medium green, approximately Cedar Green (Plate VI), covered with gray bloom. New growth is much lighter, being approximately Lettuce Green (Plate V).

*Strength.*—Very strong and rigid although slender. Capable of holding the very large flowers upright.

Foliage:

*Size.*—Up to 4 inches in length and about ¼ inch in width.

*Character.*—Curling.

*Texture.*—Substantial.

*The flower*

Size: Very large, averaging 4 inches across. It is larger than any other white carnation known to me and is ⅓ larger than its parent, Allwood's Purity, which it most resembles.

Form: Full-bodied, regular and well-balanced. Guard petals symmetrically arranged and well defined.

Petalage: Average 50 to 55 petals.

Color: Pure white to faint cream in the depths of the shadows, turning creamy when old.

Fragrance: Extremely rich clove fragrance; this feature being seldom found in a very large carnation flower.

Texture: Very substantial, enhancing both size and keeping qualities.

Calyx: Very tough and non-splitting. Broad at base. Claws wide and very resilient. These features are very important in a large flower.

Pistils: Pure white, short, usually 2-pronged.

Stamens: Few and insignificant.

Keeping quality: Excellent. Better than any other white carnation known to me. This makes it an excellent shipping variety.

Having thus disclosed my invention, I claim:

The new and distinct variety of carnation plant, substantially as herein shown and described, characterized particularly by its freedom of growth; its quick and prolific production of large flowers, the very large size, symmetrical, full-bodied form, good substance, and excellent keeping qualities of its flowers; the broad non-splitting calyx with exceedingly resilient claws; and the intense clove fragrance—both of the latter qualities being particularly unusual for so large a carnation flower.

MONTAGU CHARLES ALLWOOD.

No references cited.